_United States Patent_ [19]

Kwong

[11] Patent Number: 5,794,624

[45] Date of Patent: Aug. 18, 1998

[54] METHOD AND SYSTEM FOR THE FAST DETERMINATION OF EKG WAVEFORM MORPHOLOGY

[75] Inventor: Manlik Kwong, Corvallis, Oreg.

[73] Assignee: Hewlett-Packard Company, Palo Alto, Calif.

[21] Appl. No.: 792,604

[22] Filed: Jan. 31, 1997

[51] Int. Cl.$^6$ ............................................. A61B 5/0402
[52] U.S. Cl. .............................................. 128/702
[58] Field of Search .................... 128/702, 696, 128/703, 704, 920, 923

[56] References Cited

U.S. PATENT DOCUMENTS

| | | | |
|---|---|---|---|
| 3,940,692 | 2/1976 | Neilson | 128/702 |
| 4,124,894 | 11/1978 | Vick et al. | 128/703 |
| 4,589,420 | 5/1986 | Adams et al. | 128/702 |
| 5,215,098 | 6/1993 | Steinhaus et al. | 128/702 |
| 5,240,009 | 8/1993 | Williams | 128/702 |

_Primary Examiner_—William E. Kamm
_Assistant Examiner_—Kennedy J. Schaetzle

[57] ABSTRACT

A method and system for providing the improved automated diagnosis of heart function on the basis of electrocardiographic data in a much less computationally intensive manner than has been done previously. The objectives of the method and system are accomplished by the following steps. First, waveform templates known to be indicative of heart conditions of interest are collected. Second, a data compression algorithm is used to extract from the collected waveforms only that data essential to making an accurate diagnosis of the conditions with which the templates are associated; the resulting data is used to construct waveforms referred to as reduced-data electrocardiographic waveform templates. Third, the reduced-data electrocardiographic waveform templates are then correlated with the patient's electrocardiographic waveforms and on the basis of the results of the correlation a diagnosis is rendered.

10 Claims, 6 Drawing Sheets

METHOD AND SYSTEM FOR THE FAST DETERMINATION OF EKG WAVEFORM MORPHOLOGY

BACKGROUND

1. Technical Field:

The present invention relates, in general, to an improved method and system for providing automated diagnosis of heart function and, in particular, to an improved method and system for providing automated diagnosis of heart function and which is capable of making such diagnosis in a much less computationally intensive manner than has been done previously. Still more particularly, the present invention relates to an improved method and system for providing automated diagnosis of heart function and which is capable of making such diagnosis in a much less computationally intensive manner than has been done previously by extracting from diagnostic electrocardiographic waveform templates only that data necessary to make an accurate diagnosis and using the resulting reduced-data electrocardiographic waveform templates to make a diagnosis.

2. Description of Related Art:

The present invention presents an improvement to the prior art methods and systems for automatically diagnosing heart function on the basis of a patient's electrocardiographic waveform data. The improvement is embodied in a method and system for making the automated diagnosis in a much more computationally efficient manner. In the methods and systems existing within the prior art, automated diagnosis is made by cross-correlating a patient's electrocardiographic data with full-fidelity waveform templates. The present invention improves upon the prior art in that it sets forth an innovative way for generating and using reduced-data waveform templates such that the automated diagnosis can be done in a much more computationally efficient manner, which effectively gives an order of magnitude increase in the speed at which such automated diagnosis can be made.

Both the prior art and the present invention utilize certain specific electrical signals derived from a device for monitoring heart function known as the electrocardiograph. In order to understand how these certain specific electrical signals are utilized, it is helpful to have a basic understanding of the electrocardiograph and to what the certain specific electrical signals refer. Accordingly, as an aid to understanding the electrocardiograph, the discussion below presents a brief description of (1) the electrochemical and mechanical operation of the heart, (2) how the electrochemical operation of the heart is transduced into electrical energy which is then used by the electrocardiograph to graphically denote the mechanical operation of the heart, and (3) how the certain specific electrical signals (or "leads") are derived from the electrocardiograph.

The mechanical events of the heart are preceded and initiated by the electrochemical activity of the heart (i.e., the propagation of the action potential). There is a device which transforms the electrochemical activity of the heart into a form visible to the human eye: the electrocardiograph, which produces a visual representation of the electrochemical activity of the heart. The visual representation is known as the electrocardiogram (EKG).

During an EKG, electrodes are attached to the body surface. The electrodes are specially treated to allow the charge carriers within the electrodes (electrons) to communicate with the charge carriers within the body (ions) via electrochemical exchange. Attaching electrodes to the body surface allows the voltage changes within the body to be recorded after adequate amplification of the signal. A galvanometer within the EKG machine is used as a recording device. Galvanometers record potential differences between two electrodes. The EKG is merely the recording of differences in voltage between two electrodes on the body surface as a function of time, and is usually recorded on a strip chart. When the heart is at rest, diastole, the cardiac cells are polarized and no charge movement is taking place. Consequently, the galvanometers of the EKG do not record any deflection. However, when the heart begins to propagate an action potential, the galvanometer will deflect since an electrode underneath which depolarization has occurred will record a potential difference from a region on the body under which the heart has not yet depolarized.

A complete heart cycle is known as a heartbeat. On an EKG, a normal heartbeat has a distinctive signal. Initially, the galvanometer notes a relatively short duration rounded positive deflection (known as the P wave), which is believed to be caused by atrial depolarization. Subsequent to this, there is a small but sharp negative deflection (known as the Q wave). Next, there is a very large and sharp positive deflection (known as the R wave), after which there is a sharp and large negative deflection (known as the S wave). When these waves are taken together, they are known as the QRS complex. The QRS complex is believed to be caused by ventricular depolarization. Subsequent to the QRS complex, is a relatively long duration rounded positive deflection (known as the T wave), which is believed to be caused by ventricular repolarization.

The EKG, in practice, uses many sets of electrodes. But these electrodes are so arranged on the surface of the body such that the signal received will have the similar shape as that just described. Well-known bipolar pairs of electrodes are typically located on a patient's right arm (RA), left arm (LA), right leg (RL) (commonly used as a reference), and left leg (LL). Monopolar electrodes referenced properly are referred to as V leads and are positioned anatomically on a patient's chest according to an established convention. In heart monitoring and diagnosis, the voltage differential appearing between two such electrodes or between one electrode and the average of a group of other electrodes represents a particular perspective of the heart's electrical activity and is generally referred to as the EKG. Particular combinations of electrodes are called leads. For example, the leads which may be employed in a standard twelve-lead electrocardiogram system are:

Lead I=(LA-RA)
Lead II=(LL-RA)
Lead III=(LL-LA)
Lead V1=V1-(LA+RA+LL)/3
Lead V2=V2-(LA+RA+LL)/3
Lead V3=V3-(LA+RA+LL)/3
Lead V4=V4-(LA+RA+LL)/3
Lead V5=V5-(LA+RA+LL)/3
Lead V6=V6-(LA+RA+LL)/3
Lead aVF=LL-(LA+RA)/2
Lead aVR=RA-(LA+LL)/2
Lead aVL=LA-(RA+LL)/2

Thus, although the term "lead" would appear to indicate a physical wire, in electrocardiography the term actually means the electrical signal taken from a certain electrode arrangement as illustrated above.

Over the years, health care professionals have built up a body of knowledge wherein they have learned to coordinate variations in and data from the EKG with different diseases and heart defects. Formally, this process of coordinating is known as "electrocardiography."

Machines have been created which have automated many of the functions traditionally performed by human electrocardiologists. One of the most common ways by which engineers have been able to create these machines has been to approximate the diagnoses of the human cardiologists via the use of one or more waveform templates. The one or more waveform templates are generally pre-stored waveform templates indicative of certain heart conditions of interest.

The way in which such templates are typically used is as follows. First, a multi-lead electrocardiograph is affixed to a particular patient and an electrocardiogram is begun. Second, an EKG waveform is obtained from one or more leads. Third, one or more waveform templates indicative of certain heart conditions of interest are cross correlated with the patient's stored waveform. The waveform template is cross correlated with the patient's EKG waveform by "sweeping" the waveform template over the received waveform and keeping track of how well the waveform template intersected with the patient's EKG waveform. If it is determined that the base template correlated well with the patient's received data, then it is determined that the patient has the heart condition associated with the template.

This correlation technique for automating diagnosis works very well, but is computationally intensive. That is, both the template and the waveform are typically sampled at as high a rate as possible in order to assure that the most salient data is not inadvertently excluded (that is, since it is not readily apparent what data within the template is truly indicative of the heart condition of interest, the standard technique is to retain as much of the data as possible so that whatever data is necessary to make the diagnosis is still contained within the waveform). Unfortunately, while this results in an accurate diagnosis, it also includes a great deal of redundant data which greatly increases computational overhead.

Thus, it is apparent that a need exists for the present invention: a method and system capable of extracting from the waveform templates that data necessary to make an accurate diagnosis, and discarding that data not necessary for accurate diagnosis, so that an accurate diagnosis can be made in a much less computationally intensive and thus much faster manner.

SUMMARY OF THE INVENTION

It is therefore one object of the present invention to provide an improved method and system for providing automated diagnosis of heart function.

It is another object of the present invention to provide an improved method and system for providing automated diagnosis of heart function and which is capable of making such diagnosis in a much less computationally intensive manner than has been done previously.

It is yet another object of the present invention to provide an improved method and system for providing automated diagnosis of heart function and which is capable of making such diagnosis in a much less computationally intensive manner than has been done previously by extracting from diagnostic electrocardiographic waveform templates only that data necessary to make an accurate diagnosis and using the resulting reduced-data electrocardiographic waveform templates to make a diagnosis.

The foregoing objects are achieved as is now described. A method and system for providing improved automated diagnosis of heart function in a much less computationally intensive manner than has been done previously. The objectives of the method and system are accomplished by the following steps. First, waveform templates known to be indicative of heart conditions of interest are collected. Second, a data compression algorithm is used to extract from the collected waveforms only that data essential to making an accurate diagnosis of the conditions with which the templates are associated; the resulting data is used to construct waveforms referred to as reduced-data electrocardiographic waveform templates. Third, the reduced-data electrocardiographic waveform templates are then correlated with the patient's electrocardiographic waveforms and on the basis of the results of the correlation a diagnosis is rendered.

The above as well as additional objects, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

DETAILED DESCRIPTION OF PREFERRED EMBODIMENT

The following description describes a method and system which utilizes and acts upon waveforms appearing within a patient's electrocardiographic data. Any such discussion is complicated by the fact that electrocardiogram is taken there are generally twelve leads (electrical signals) within which appear some version of the electrical signal representative of the patient's heart function. Furthermore, successive heartbeat waveforms appear within each lead on successive heartbeats.

In order to avoid confusion, the following discussion describes the method and system of the present invention as it relates to one lead. It is to be understood that in the preferred embodiment the method and system can be simultaneously applied to one or more of the electrocardiographic leads present. In addition, the discussion below describes diagnosis based upon one waveform, but it is to be understood that the diagnosis can be repeated for some or all of the electrocardiographic waveforms appearing in succession within each lead.

Figure 1:
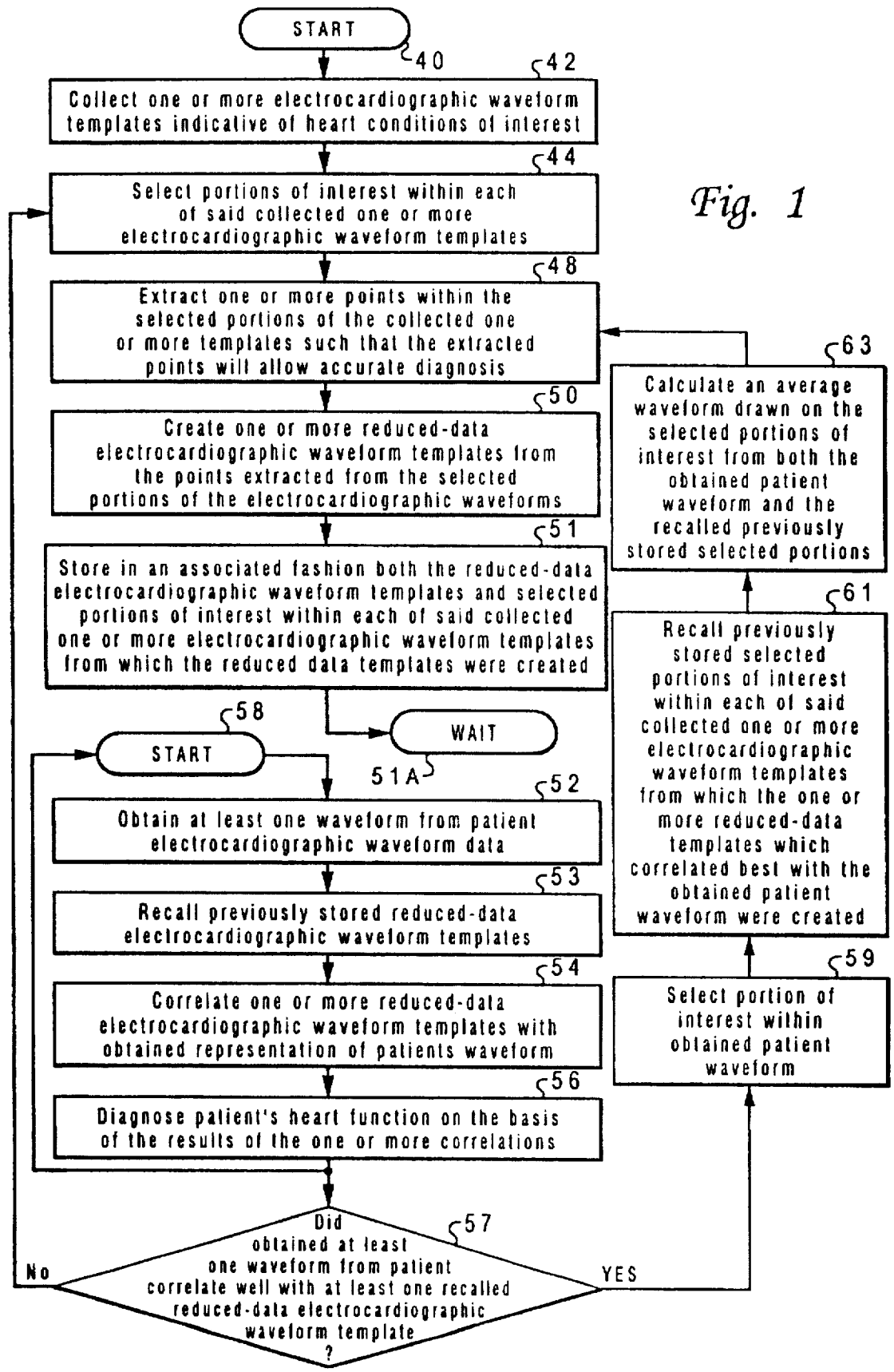
FIG. 1 is a high-level logic flowchart depicting the method and process of the present invention.

With reference now to the figures and in particular with reference now to FIG. 1, it can be seen that FIG. 1 is a high-level logic flowchart depicting the method and process of the present invention. Method step 40 illustrates the start of the process. Method step 42 shows the collection of one or more electrocardiographic waveform templates indicative of heart conditions of interest. In the preferred embodiment, what are actually collected are values of the electrocardiographic waveform data at discrete instances in time, but the time sampling is so fast that for most conceptual purposes the time-sampled waveforms can be thought of and discussed "as if" the waveforms were in their analog form. Accordingly, most of the discussion below treats the discretely sampled waveforms "as if" they were analog, with the understanding that such is done only for conceptual clarity since in actuality what is being worked with is not the analog waveform, but rather a discretely time sampled version of it.

The collected one or more waveforms are then designated as collected electrocardiographic waveform templates indicative of one or more heart conditions of interest. In the preferred embodiment, the condition of interest is whether the patient's heartbeat is becoming irregular, but it is also envisioned that such waveforms could be scanned to detect other conditions, such as Acute Myocardial Infarction, by comparing the collected waveforms with pre-stored reference templates indicative of such.

Method step 44 depicts the process of the selection of one or more portions of interest within each of the collected electrocardiographic waveform templates indicative of one or more heart conditions of interest. In the preferred embodiment, the selected portions of interest are those portions making up the QRST complex.

Method step 48 shows the extraction of one or more points within the selected one or more portions of interest within each of the collected electrocardiographic waveform templates. In the preferred embodiment, these points are extracted from the discrete time approximation of the continuous time QRST complex, but it is also envisioned that such points could be extracted from the time sampled versions of other selected one or more portions of interest within each of the collected electrocardiographic waveform templates. The extraction of method step 48 is done with a process for extracting, which in the preferred embodiment is a modified FAN data compression algorithm. The FAN data compression algorithm is well known by those skilled in the art. The FAN data compression algorithm extracts from a full-fidelity waveform a set of discrete data points which are subsequently used to generate a facsimile of the original full-fidelity waveform. The process for extracting used in the preferred embodiment is the FAN data compression algorithm modified such that the discrete data points extracted by the FAN data compression algorithm are retained.

Method step 50 depicts the creation of one or more reduced-data electrocardiographic waveform templates from the extracted points of method step 48. Such a reduced-data electrocardiographic waveform template will often look like a dot-to-dot tracing as is shown by the asterisks 101 in FIG. 2. The reason that this dot-to-dot tracing still yields accurate diagnoses is that the process for extracting the points used in method step 48 is carefully designed such that the points extracted, or data retained, is that necessary to make an accurate diagnosis. Method step 51 illustrates the storing in memory in an associated fashion both the created one or more reduced-data electrocardiographic waveform templates and the selected portions of interest from which the created one or more reduced-data electrocardiographic waveform templates were created. In other words, this step allows one to maintain a logical association between the stored reduced-data templates and the stored selected portions of electrocardiographic waveforms that were used to create each stored reduced-data template.

After the created one or more reduced-data electrocardiographic waveform templates and selected portions of interest within each waveform from which the reduced-data templates have been created are stored (i.e. after the completion of method step 51) method step 51A shows the entering of a wait state.

Simultaneous with the proceeding of method steps 40-51A, the process begins and continues with method step 58. Method step 58 depicts the start of the second component of the process. Method step 52 depicts the obtainment of at least one electrocardiographic waveform representation from a patient's electrocardiographic waveform data. Method step 53 shows the recall from memory of the reduced-data electrocardiographic waveform templates created in method step 50 and stored in memory in method step 51. Method step 54 illustrates that the at least one electrocardiographic waveform representation from a patient's electrocardiographic waveform data is then correlated with the one or more reduced-data electrocardiographic waveform templates recalled in method step 53.

In the preferred embodiment, the method step 54 correlation of the one or more reduced-data electrocardiographic waveform templates with a patient waveform is done by using what is known as an "area of difference" technique. In the "area of difference" technique utilized what is done is that the one or more reduced-data electrocardiographic waveform templates recalled in method step 53 are discretely time shifted along a waveform. After each time shift, the value of the patient data waveform corresponding to the points in time at which data exists in the reduced-data electrocardio graphic waveform templates being correlated is subtracted from the values of the reduced-data electrocardiographic waveform templates at those same points in time, and the results of these subtractions are summed, and the resulting sum is then divided by the total number of data points where a subtraction took place. Thus, if there is an exact match between the template and the captured waveform, the sum will go to zero (because in an exact match each subtraction will yield zero). A record of the successive area of difference calculations is kept as the template is time shifted across the patient data waveform, with the lowest area of difference result being held to be indicative of the best fit obtained (since the lower the area of difference result the better the fit). This correlation operation is done for each of the one or more reduced-data electrocardiographic waveform templates recalled from memory in method step 53, and the results of such correlation operations for each of the one or more reduced-data electrocardiographic waveform templates are passed to method step 56.

Method step 56 shows the diagnosis of the patient's heart function on the basis of how well the patient's waveform data correlated with the one or more reduced-data electrocardiographic waveform templates. The diagnosis is based upon how well the one or more reduced-data electrocardiographic waveform templates correlated with the patient's waveform data. The degree of correlation required to result in a diagnosis is a variable parameter which can be set by the programmer (in the preferred embodiment, a value of 0.35 or better is deemed "good" correlation).

After the diagnosis for the heartbeat under consideration has been made (i.e. after the completion of method step 56) one branch of the process returns to method step 58 and proceeds in an iterative fashion.

Simultaneous with the iterative proceeding just referenced, after the diagnosis for the heartbeat under consideration has been made (i.e. after the completion of method step 56) another branch of the process continues with the decision block shown in method step 57. Method step 57 asks if the obtained at least one waveform from patient correlated well with one or more of the recalled reduced-data electrocardiographic waveform templates.

If the answer to the question asked in method step 57 is yes, then the obtained patient's waveform of method step 52 is used to calculate a new average waveform from which a new reduced-data electrocardiographic waveform template is produced. Method step 59 illustrates the selection of a portion of interest from within the obtained patient's waveform, which in the preferred embodiment is the QRST complex. Method step 61 shows the recall of the previously stored (method step 51) selected portions of interest within each electrocardiographic waveform template which were used to create the reduced-data template which had the best correlation (i.e. had the lowest area of difference result) with the obtained patient's waveform, which in the preferred embodiment is the recall of the selected QRST complexes which were stored in method step 51. Method step 63 depicts calculating an average waveform drawn on the recalled selected portions and the selected portion of interest from the obtained patient waveform. In the preferred embodiment what is calculated in this step is the average waveform drawn on the recalled QRST complexes along with the newly selected QRST complex newly selected from the obtained patient waveform. After this average waveform is created it is delivered to method step 48 where it (the newly calculated average waveform of method step 63) is used to create a new reduced-data electrocardiographic waveform template in method step 50. The process then proceeds as normally except that when method step 51 is reached, the newly created reduced-data electrocardiographic waveform template overwrites and replaces the reduced-data electrocardiographic waveform template which was previously created from those selected portions recalled in method step 61, and the newly selected (method step 59) portion of the waveform as well as the recalled (method step 61) previously stored selected portions are stored in association with the newly created reduced-data electrocardiographic waveform template.

Method step 63 illustrates the creation of an average waveform drawn on the selected one or more portions of interest within each of the collected electrocardiographic waveform templates. It is to be understood that method step 63 exists within the preferred embodiment, but that such step is optional in the invention. Shown is the operation of creating an "average" QRST complex drawn on every QRST complex recalled in method step 61 as well as the QRST complex selected from the obtained patient waveform. There are two ways in which this average is calculated in the preferred embodiment: direct averaging and alpha trimming. However, in both forms of averaging, it is necessary to place all waveforms on the same time baseline so that the averaging can take place. There are many possible ways to place the waveforms on the same time baseline, but in the preferred embodiment this is done by determining the P-R segment (the relatively flat segment between the end of the P wave and the beginning of the Q wave) for each selected waveform, and then aligning all waveforms about their P-R segments by ensuring that the P-R segment for each wave appears at the same time on the time baseline. With the waveforms so aligned, a reference value (e.g. t=0) is chosen and the values of each waveform at different times along the baseline are recorded (e.g., the values of the waveforms at t=20 ms, 40 ms, 60 ms, etc.). Once these values have been so determined, either direct averaging or alpha trimming can be done. In direct averaging, the values of the waveform at each time interval are simply summed and divided by the number of waveforms being averaged, which yields an average value at each sample time. In alpha trimming, essentially the same thing is done, except that at each time sample the values of the waveforms are sorted from lowest to highest, some of the outlying values (e.g. the top 20% and bottom 20%) are discarded, and then the remaining waveform values are averaged. The foregoing describes one way in which the average waveform can be obtained, but it is well known in the art that many other forms of averaging are possible. Once the averaging has been completed, average values at each time sample exist and such can be used as a discrete time approximation of the continuous time average waveform (i.e. in the preferred embodiment, no curve fitting or interpolation is done, but rather the discrete time approximation is used "as is").

In the preferred embodiment, the selected portions of the waveforms are those that make up the QRST complex. Thus, the averaging operation yields a discrete time approximation to the continuous time average QRST complex.

If the answer to the question asked in method step 57 is no, then the obtained patient's waveform is used to calculate a new reduced-data electrocardiographic waveform template. This is done by delivering the obtained patient waveform to method step 44, wherein the obtained patient waveform is treated as a collected electrocardiographic waveform template. The process then proceeds as usual from that point.

Figure 2:
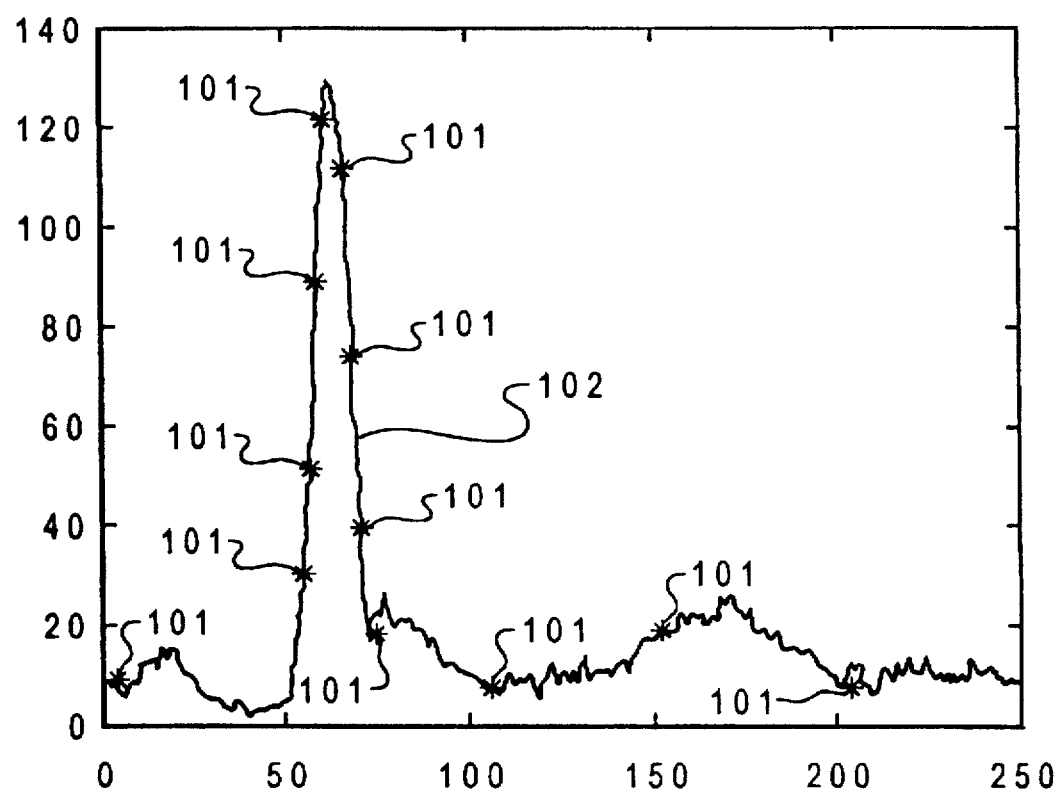
FIG. 2 is a conceptual illustration of how a reduced-data electrocardiographic waveform template can look in relation to the full-fidelity electrocardiographic waveform.

Refer now to FIG. 2, which is a conceptual illustration of how a reduced-data electrocardiographic waveform template (100 in FIGS. 2A–E) can look in relation to the full-fidelity electrocardiographic waveform 102 from which it is extracted. In FIG. 2, the critical points to be extracted from a full-fidelity waveform 102 to form a reduced-data electrocardiographic waveform template appear as asterisks 101. As can be seen from the illustration of FIG. 2, the reduced-data electrocardiographic waveform template (100 in FIGS. 2A–E) will consist of a collection of points extracted from the full-fidelity electrocardiographic waveform 102.

Figure 2A:
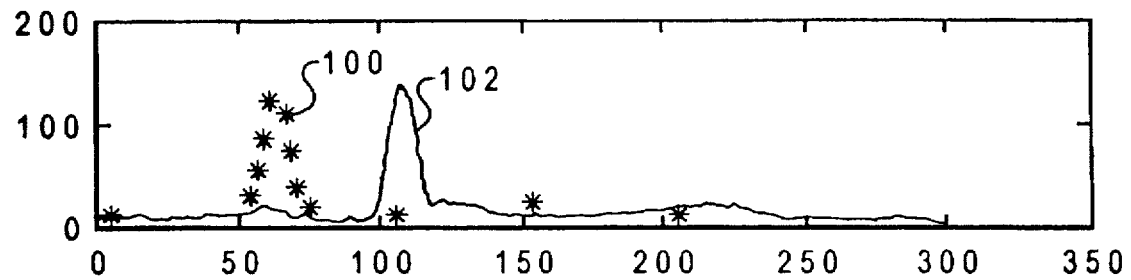
FIGS. 2A–E illustrates how a reduced-data electrocardiographic waveform template can look as it is time shifted across a patient's electrocardiographic waveform data.
Figure 2B:
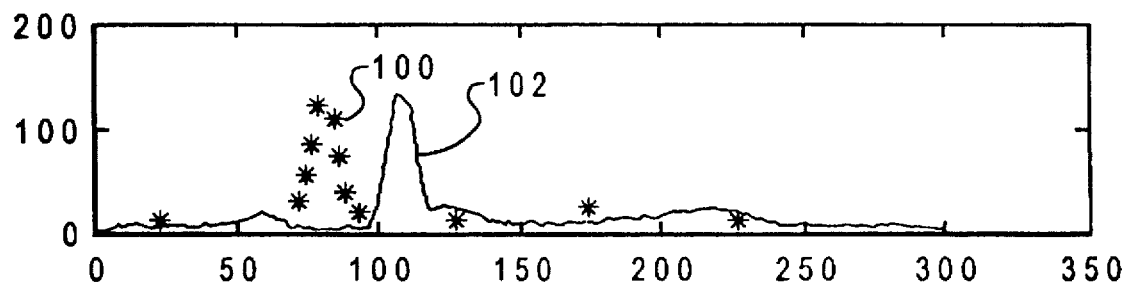
Figure 2C:
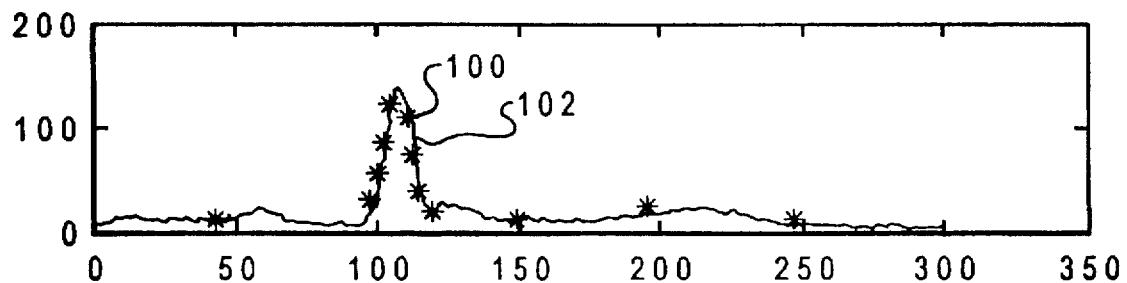
Figure 2D:
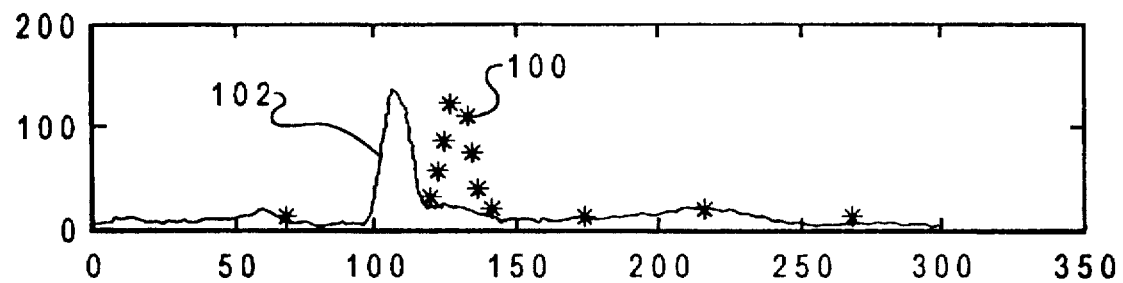
Figure 2E:
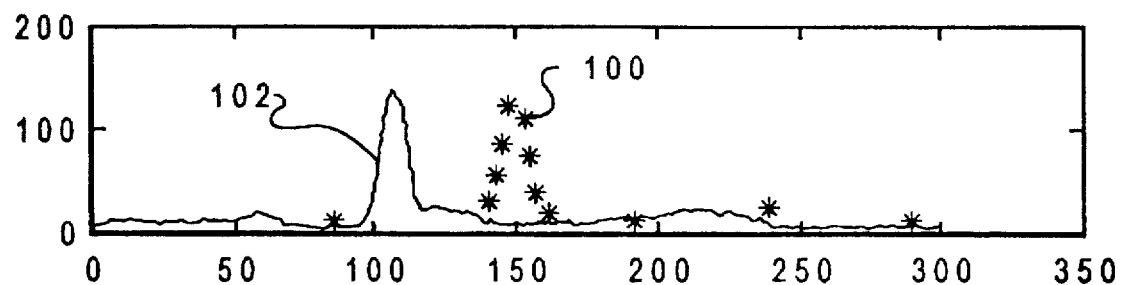

Refer now to FIGS. 2A–E, which illustrate how a reduced-data electrocardiographic waveform template can look as it is time shifted across a patient's electrocardiographic waveform data. FIGS. 2A–E is a sequence of illustrations of how one reduced-data electrocardiographic waveform template 100 (which is composed of the collection of asterisks 101 shown in FIG. 2 which represent points extracted to form the reduced-data electrocardiographic waveform template) could be time shifted across a patient's waveform data 102 to obtain correlation information; furthermore, although what is shown in the picture appears to be an analog waveform for the patient's waveform data 102, it is to be understood that in the preferred embodiment this is to be a discretely sampled representation of the analog waveform, with the discrete sample intervals being the same as the discretely sampled waveforms from which the one or more reduced data templates have been obtained. FIG. 2A shows the reduced-data electrocardiographic waveform template 100 and a patient's waveform data 102 at some time t1, at which time the area of difference calculation is done and saved, as discussed above. FIG. 2B shows the reduced-data electrocardiographic waveform template 100 and a patient's waveform data 102 at some time t2, at which time the area of difference calculation is again done and saved, as discussed above. FIG. 2C shows the reduced-data electrocardiographic waveform template 100 and a patient's waveform data 102 at some time t3, at which time the area of difference calculation is again done and saved, as discussed above. FIG. 2D shows the reduced-data electrocardiographic waveform template 100 and a patient's waveform data 102 at some time t4, at which time the area of difference calculation is again done and saved, as discussed above. FIG. 2E shows the reduced-data electrocardiographic waveform template 100 and a patient's waveform data 102 at some time t5, at which time the area of difference calculation is again done and saved, as discussed above. It can be seen that at time t3, the difference between the reduced-data electrocardiographic waveform template 100 and the patient's waveform data 102 is virtually zero since the two waveforms correlate well. It can also be seen that at times t1, t2, t4, and t5 there is fairly substantial difference between the reduced-data electrocardiographic waveform template 100 values and the patient's waveform data 102 values, so the area of difference calculations will yield relatively large numbers at these times. Hence, in this instance the area of difference calculation retained in method step 54 and passed to method step 56, as discussed above, would be that obtained at t3, since such would be the smallest number and thus the indicator of best correlation as the reduced-data electrocardiographic waveform template 100 was swept across the patient's waveform data 102.

Additionally, it can be seen from FIG. 2 that only a few points from the virtually infinite number of possible points have been saved in the reduced-data electrocardiographic waveform template. The saved points are those necessary to get an accurate diagnosis of the heart condition of interest. What points are to be saved is determined by the process for extracting (which in the preferred embodiment, as discussed above, is a modified FAN data compression algorithm), which is created by the method and process depicted in FIG. 3.

Figure 3:
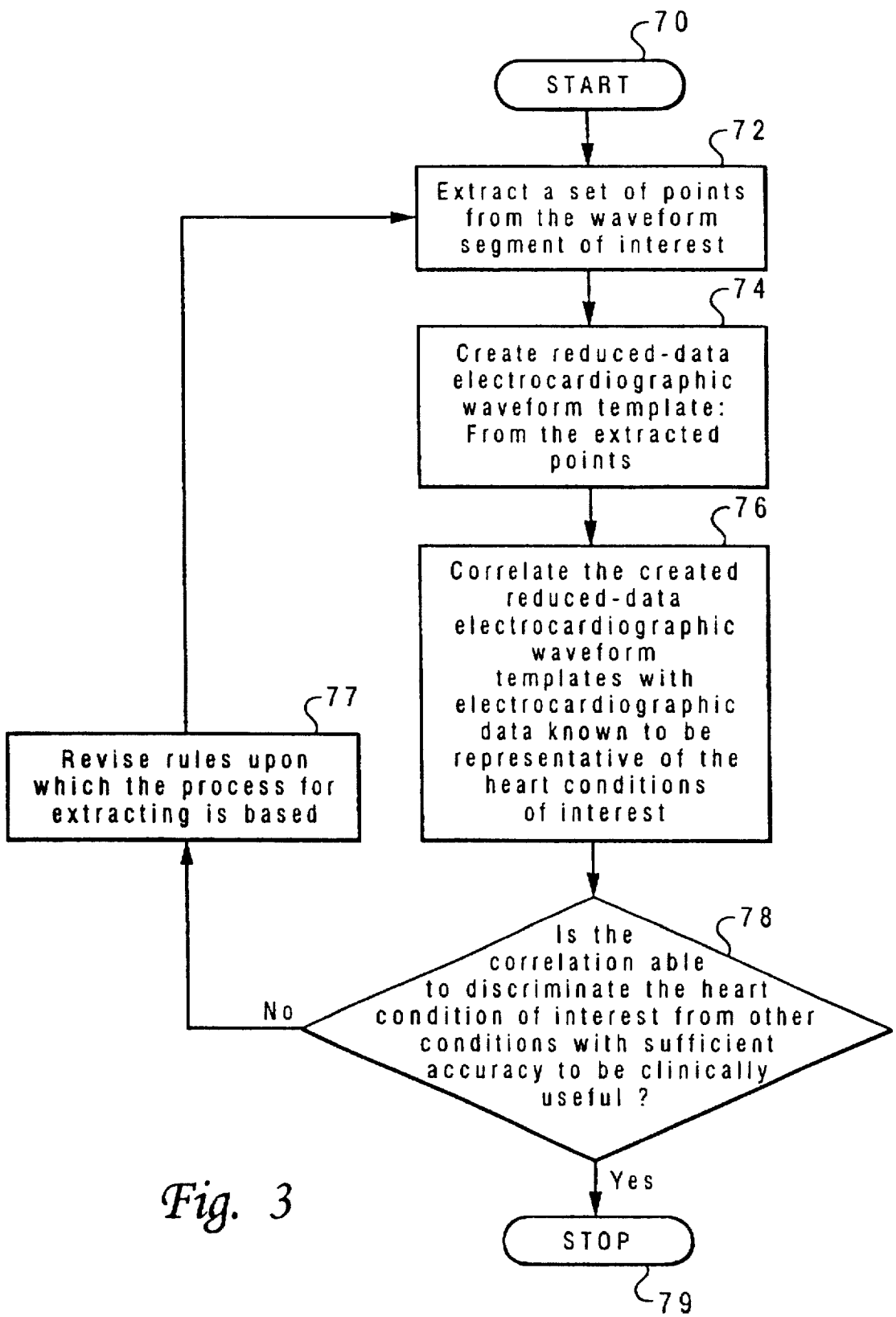
FIG. 3 is a high-level logic flowchart depicting the method and process for the creation of the process by which data points are extracted.

Referring now to FIG. 3, it can be seen that FIG. 3 is a high-level logic flowchart depicting the method and process for the creation of the process by which data points are extracted as in method step 48. Method step 70 depicts the beginning of the process. Method step 72 illustrates the extraction of a set of points from the waveform segment of interest by use of a rules-based process. Method step 74 shows the creation of a reduced-data electrocardiographic waveform template from the extracted points. Method step 7 depicts the correlation of the created reduced-data electrocardiographic waveform templates with various electrocardiographic waveforms known to be representative of various heart conditions of interest. Method step 78 illustrates the determination of how well the correlation was able to discriminate certain heart conditions of interest from other conditions. If it is determined that the correlation was able to adequately discriminate certain heart conditions of interest from other heart conditions (i.e., has both sufficient sensitivity and selectivity to be clinically useful), then the process for extracting used in method step 72 is deemed acceptable, and such process of extracting is saved for later use within the present invention. However, if it is determined in method step 78 that the correlation did not adequately discriminate, the rules upon which the process for extracting is based are revised as shown in method step 77, and method steps 72–78 are repeated. Method step 79 depicts the ending of the process, which occurs when the process for extracting yields a reduced-data waveform template which gives adequate discrimination of the heart conditions of interest from other conditions.

Figure 4:
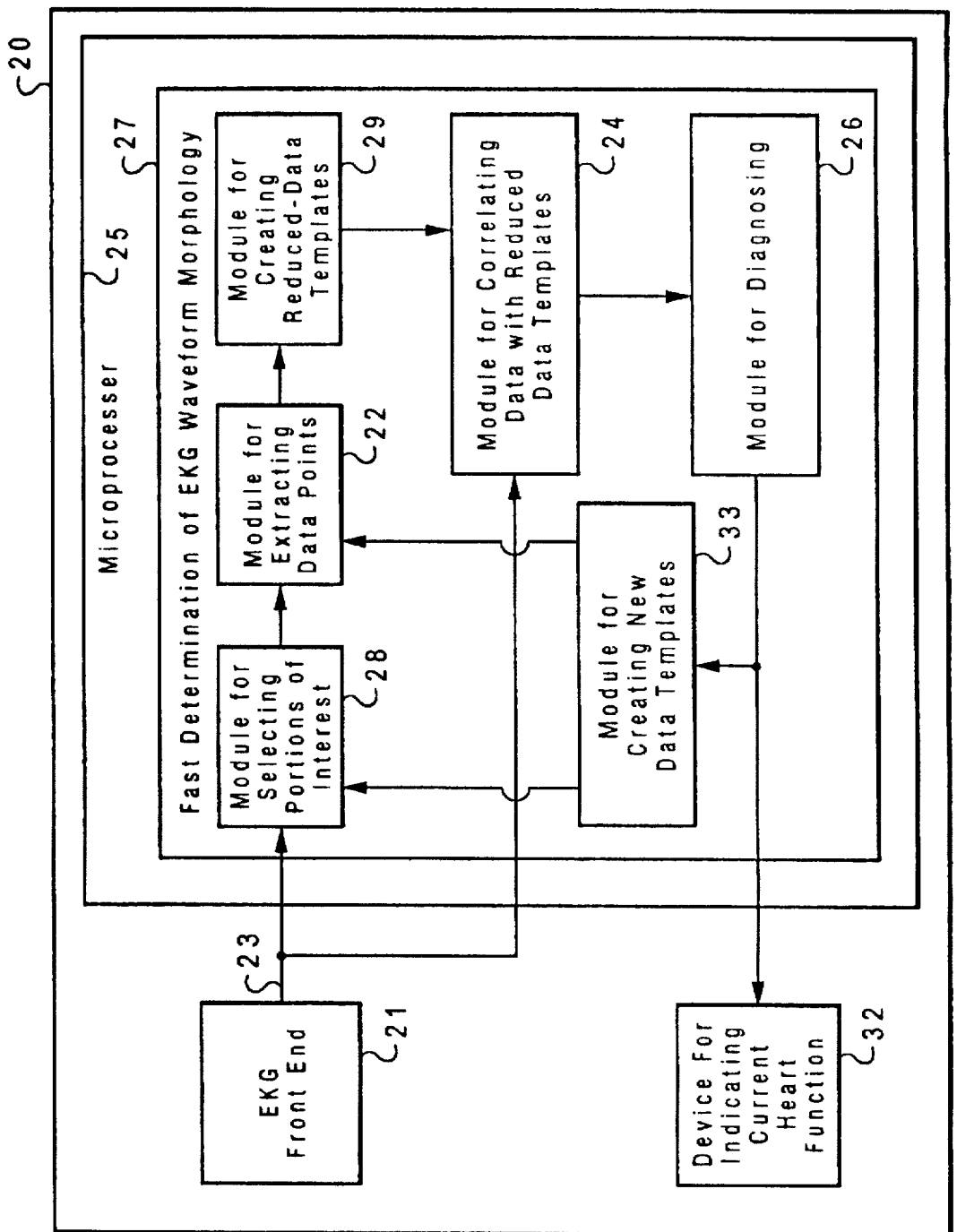
FIG. 4 illustrates a high-level schematic view of a system for implementing the present invention.

Referring now to FIG. 4, there is depicted a high level schematic view of a system for implementing the present invention. FIG. 4 presents the system as a set of programs running on computer machinery, but those skilled in the art will recognize that the functions described here as software could also be implemented in hardware or firmware. Illustrated is a patient 14, to whom a number of electrocardiographic electrodes 16 are affixed. Electrocardiographic electrodes 16 are connected via conducting cables 18 to EKG monitor 20. EKG monitor 20 produces EKG waveform signals which are then fed to EKG front end 21. EKG front end 21 signal conditions and filters the EKG waveform signals and then A/D converts and outputs a stream of discretely sampled EKG waveforms, which for simplicity of understanding will simply be referred to as stream of EKG waveforms 23.

The leading waveform from the stream of EKG waveforms 23 is delivered to microprocessor 25 which is running fast determination of EKG waveform morphology software module 27, within which is contained module for selecting portions of interest within waveform templates 28, module for extracting data points 22, module for creating reduced-data templates 29, module for correlating patient's data with reduced-data templates 24, module for diagnosing 26, and module for creating new data templates 33.

The leading waveform from the stream of EKG waveforms 23 is delivered to module for selecting portions of interest within waveform templates 28. Module for selecting portions of interest within waveform templates 28 contains programming sufficient to carry out method step 44.

Once the portions of interest have been selected module for selecting portions of interest within waveform templates 28 passes the selected portions of interest to module for extracting data points 22. Module for extracting data points 22 contains programming sufficient to do the same function as that of method step 48.

Once module for extracting data points 22 has extracted the appropriate points, module for extracting data points 22 passes the points to module for creating reduced-data templates 29, which contains programming sufficient to produce a reduced-data template from the extracted points, and then record, and store each such reduced-data waveform template produced as is done in method steps 48–51.

Module for correlating patient's data with reduced-data templates 24 receives stream of EKG waveforms 23. Module for correlating patient's data with reduced-data templates 24 contains programming sufficient to effectuate method steps 58, 53, and 54. For each successive waveform in stream of EKG waveforms 23, module for correlating patient's data with reduced-data templates 24 queries module for creating reduced-data templates 29 for the reduced-data templates currently stored in memory. In response to this query, module for creating reduced-data templates 29 delivers the stored reduced-data electrocardiographic waveform templates to module for correlating patient's data with reduced-data templates 24 which contains programming sufficient to effect the correlation of method step 54. Once such correlation has been done for each reduced-data template received from module for creating reduced-data templates 29, module for correlating patient's data with reduced-data templates 24 passes the correlation results for each type waveform to module for diagnosing 26 which contains programming sufficient to effectuate method step 56 and the loop back from method step 56 to method step 58. Module for diagnosing 26 then uses the correlation results to output a result to device for indicating current heart function 32, which indicates the occurrence of current heart function by appropriate means such as a flashing light, a buzzer or any other alarm which may be deemed useful.

Simultaneous with the foregoing output to device for indicating current heart function 32, module for diagnosing 26 also delivers the correlation results for each reduced-data electrocardiographic waveform template to module for creating new data templates 33. Module for creating new data templates 33 contains programming sufficient to carry out method steps 57, 59, 61, and 63, and either outputs the obtained patient's waveform to module for selecting portions of interest within waveform templates 28 or a newly calculated average selected portion of waveform to module for extracting data points 22, dependent upon the results of the programming steps correspondent to the decision block of method step 57. Module for selecting portions of interest within waveform templates 28 contains programming to receive the obtained patient's waveform and execute method steps 48–51. Module for extracting data points 22 contains programming sufficient to receive the newly calculated average selected portion of waveform and execute method steps 48–51 in the modified fashion described when such method steps are executed following method steps 59, 61, and 63 as was discussed in reference to FIG. 1.

While an illustrative embodiment has been particularly shown and described, it will be understood by those skilled in the art that various changes in form and detail may be made therein without departing from the spirit and scope of the illustrative embodiment.

What is claimed is:

1. A method for providing improved automated diagnosis of heart function on the basis of electrocardiographic data, said method comprising the steps of:

collecting one or more electrocardiographic waveform templates known to be indicative of heart conditions of interest;

selecting portions of said collected one or more electrocardiographic waveform templates with said selected portions being especially identified with said heart conditions of interest;

creating one or more reduced-data electrocardiographic waveform templates from said selected portions of said collected one or more electrocardiographic waveform templates by extracting from said selected portions of said collected one or more electrocardiographic waveform templates only predetermined points; and diagnosing a patient's heart function by correlating said created one or more reduced-data electrocardiographic waveform templates with said patient's electrocardiographic waveform data.

2. The method of claim 1 wherein said step of collecting one or more electrocardiographic waveform templates known to be indicative of heart conditions of interest further comprises the steps of:

obtaining electrocardiographic waveform data from a plurality of patients;

determining which specific waveforms within said obtained electrocardiographic waveform data from a plurality of patients are indicative of said heart conditions of interest; and collecting as said one or more electrocardiographic waveform templates known to be indicative of heart conditions of interest those specific waveforms within said electrocardiographic waveform data from a plurality of patients which are determined to be indicative of said heart conditions of interest.

3. The method of claim 1 wherein said step of selecting portions of said collected one or more electrocardiographic waveform templates further comprises the steps of:

identifying one or more critical data points within said collected one or more electrocardiographic waveform templates such that said identified one or more critical data points have high discriminating power with respect to the existence of said heart conditions of interest with which said collected one or more electrocardiographic waveform templates are associated; and in response to said identifying step, selecting those portions of said collected one or more electrocardiographic waveform templates containing said identified one or more critical data points.

4. The method of claim 1 wherein said step of creating one or more reduced-data electrocardiographic waveform templates from said selected portions of said collected one or more electrocardiographic waveform templates by extracting from said selected portions of said collected one or more electrocardiographic waveform templates only predetermined points further comprises the steps of:

extracting one or more points within said selected portions of said collected one or more electrocardiographic waveform templates such that said extracted one or more points allow accurate diagnosis of said heart conditions of interest with which said selected portions of said collected one or more electrocardiographic waveform templates are identified; and creating said one or more reduced-data electrocardiographic waveform templates from said extracted one or more points.

5. The method of claim 1 wherein said step of diagnosing a patient's heart function by correlating said created at least one reduced-data electrocardiographic waveform templates with said patient's electrocardiographic waveform data further comprises the steps of:

obtaining a representation of at least one waveform from said patient's electrocardiographic waveform data;

correlating said one or more reduced-data electrocardiographic waveform templates with said obtained representation of said at least one waveform from said patient's electrocardiographic waveform data; and in response to the results of said correlating step, diagnosing said patient's heart function.

6. A system for providing improved automated diagnosis of heart function on the basis of electrocardiographic data, said system comprising:

means for collecting one or more electrocardiographic waveform templates known to be indicative of heart conditions of interest;

means for selecting portions of said collected one or more electrocardiographic waveform templates with said selected portions being especially identified with said heart conditions of interest;

means for creating one or more reduced-data electrocardiographic waveform templates from said collected one or more electrocardiographic waveform templates by extracting from said selected portions of said collected one or more electrocardiographic waveform templates only predetermined points; and means for diagnosing a patient's heart function by correlating said created one or more reduced-data electrocardiographic waveform templates with said patient's electrocardiographic waveform data.

7. The system of claim 6 wherein said means for collecting one or more electrocardiographic waveform templates known to be indicative of heart conditions of interest further comprises:

means for obtaining electrocardiographic waveform data from a plurality of patients;

means for determining which specific waveforms within said obtained electrocardiographic waveform data from a plurality of patients are indicative of said heart conditions of interest; and means for collecting as said one or more electrocardiographic waveform templates known to be indicative of heart conditions of interest those specific waveforms within said electrocardiographic waveform data from a plurality of patients which are determined to be indicative of said heart conditions of interest.

8. The system of claim 6 wherein said means for selecting portions of said collected one or more electrocardiographic waveform templates further comprises:

means for identifying one or more critical data points within said collected one or more electrocardiographic waveform templates such that said identified one or more critical data points have high discriminating power with respect to the existence of said heart conditions of interest with which said collected one or more electrocardiographic waveform templates are associated; and means, responsive to said means for identifying, for selecting those portions of said collected one or more electrocardiographic waveform templates containing said identified one or more critical data points.

9. The system of claim 6 wherein said means for creating one or more reduced-data electrocardiographic waveform templates from said selected portions of said collected one or more electrocardiographic waveform templates by extracting from said selected portions of said collected one or more electrocardiographic waveform templates only predetermined points further comprises:

means for extracting one or more points within said selected portions of said collected one or more electrocardiographic waveform templates such that said extracted one or more points allow accurate diagnosis of said heart conditions of interest with which said selected portions of said collected one or more electrocardiographic waveform templates are identified; and means for creating said one or more reduced-data electrocardiographic waveform templates from said extracted one or more points.

10. The system of claim 6 wherein said means for diagnosing a patient's heart function by correlating said created at least one reduced-data electrocardiographic waveform templates with said patient's electrocardiographic waveform data further comprises:

means for obtaining a representation of at least one waveform from said patient's electrocardiographic waveform data;

means for correlating said one or more reduced-data electrocardiographic waveform templates with said obtained representation of said at least one waveform from said patient's electrocardiographic waveform data; and means, responsive to said means for correlating, for diagnosing said patient's heart function.

\* \* \* \* \*